United States Patent [19]
Adam et al.

[11] Patent Number: 6,113,527
[45] Date of Patent: Sep. 5, 2000

[54] DIAZA-SPIRO[3,5] NONANE DERIVATIVES

[75] Inventors: Geo Adam, Schopfheim, Germany; Andrea Cesura, Basel, Switzerland; François Jenck, Riedisheim, France; Sabine Kolczewski, Lörrach, Germany; Stephan Röver, Inzlingen, Germany; Jürgen Wichmann, Steinen, Germany

[73] Assignee: Hoffmann-La Roche Inc., Nutley, N.J.

[21] Appl. No.: 09/330,851

[22] Filed: Jun. 11, 1999

[30] Foreign Application Priority Data

Jun. 12, 1998 [EP] European Pat. Off. ............... 98110804

[51] Int. Cl.[7] .................... A61K 31/44; C07D 221/20
[52] U.S. Cl. .............................. 574/278; 546/16
[58] Field of Search ................. 514/278; 546/16

[56] References Cited

U.S. PATENT DOCUMENTS 5,986,097 11/1999 Palermo et al. ................. 546/16

OTHER PUBLICATIONS

Manhas et al., "Studies on Lactams–XII", *Tetrahedron*, vol. 25, No. 18, pp. 4421–4426 (1969).
Reinscheid et al., "Structures that Delineate Orphanin FQ and Dynorphin A Pharmacological Selectives", *Journal of Biological Chemistry*, vol. 273, No. 3, pp. 1490–1495 (1998).
Julius, *Nature* 377:476 (1995).
Meunier, *Eur. J. Pharmacol.*, 340: 1–15 (1997).
Henderson et al., *Trends Pharmacol. Sci.*, 18:293–300 (1997).
Mogil et al., *Neuroscience*, 75:333–337 (1996).
Vanderah et al., *Eur. J. Pain*, 2:267–280 (1998).
Jenck et al., *Proc. Natl. Acad. Sci.*, USA, 94:14854–14858 (1997).
Pomonis et al., *Neuroreport*, 8:369–371 (1996).
Manabe et al., *Nature*, 394:577–581 (1998).
Peruso et al. *J. Neuroimmmuno*, 81:184–192 (1998).
Porro et al., *Prog. Clin. Biol. Res.* 397:315–325 (1998).
Benzow et al., *Febs Lett.* 347:284–288 (1994).
Cheng et al., *Biochem. Pharmacol.*, 22:3099–3108 (1973).

*Primary Examiner*—Amelia Owens
*Attorney, Agent, or Firm*—George W. Johnston; Dennis P. Tramaloni; Joseph P. Kirk, Jr.

[57] ABSTRACT

The invention relates to compounds of the general formula

I

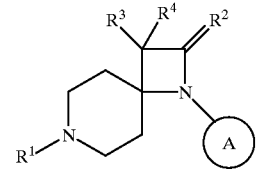

wherein $R^1$ is $C_{6-12}$-cycloalkyl, optionally substituted by lower alkyl or C(O)O lower alkyl, indan-1-yl or indan-2-yl, optionally substituted by lower alkyl; acenaphthen-1-yl; bicyclo[3.3.1]non-9-yl, octahydro-inden-2-yl; 2,3-dihydro-1H-phenalen-1-yl; 2,3,3a,4,5,6-hexahydro-1H-phenalen-1-yl, decahydro-azulen-2-yl; bicyclo[6.2.0]dec-9-yl; decahydro-naphthalen-1-yl, decahydro-naphthalen-2-yl; tetrahydro-naphthalen-1-yl, tetrahydro-naphthalen-2-yl or 2-oxo-1,2-diphenyl-ethyl;

$R^2$ is =O or hydrogen, $R^3$ is hydrogen, isoindolyl-1,3-dione, lower alkoxy, lower alkyl, amino, benzyloxy, $-CH_2OR^5$ or $-CH_2N(R^5)_2$;

$R^4$ is hydrogen or $-CH_2OR^5$;

$R^5$ is hydrogen or lower alkyl;

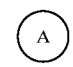

is cyclohexyl or phenyl, optionally substituted by lower alkyl, halogen or alkoxy; to racemic mixtures and their corresponding enantiomers and or pharmaceutically acceptable acid addition salts thereof.

The compounds of the present invention are agonists of the orphamin FQ (OFQ) receptor and therefore useful in the treatment of diseases, related to this receptor.

17 Claims, No Drawings

DIAZA-SPIRO[3,5] NONANE DERIVATIVES

FIELD OF THE INVENTION

This invention relates to diaza-spiro[3.5]nonane derivatives particularly wherein $R^1$ is $C_{6-9}$-cycloalkyl which may be substituted or unsubstituted or wherein $R^1$ is decahydronapthalen-2-yl and compositions thereof.

BACKGROUND

OFQ, a heptadeca-peptide, has been isolated from rat brain and is a natural ligand to a G-protein coupled receptor (OFQ-R), found at high levels in brain tissue. OFQ exhibits agonistic activity at the OFQ-R both in vitro and in vivo.

Julius (Nature 377,476, [1995]) discusses the discovery of OFQ noting that this peptide shares greatest sequence homology with dynorphin A, an established endogenous ligand for opioid receptors. OFQ inhibits adenylate cyclase in CHO(LC 132+) cells in culture and induces hyperalgesia when administered intracerebroventricularly to mice. The pattern of results indicate that this heptadecapeptide is an endogenous agonist of the LC 132 receptor and it appears to have pronociceptive properties. It has been described that when injected intracerebroventricularly in mice, OFQ slowes down locomotive activity and induces hyperalgesia and it has been concluded that OFQ may act as a brain neurotransmitter to modulate nociceptive and locomotive behavior.

It has been found that the compounds of the present invention interact with the orphanin FQ (OFQ) receptor and consequently are useful in the treatment of a variety of psychiatric, neurological and physiological disorders.

In the following references these indications have been described:

Nociceptin/orphanin FQ and the opioid receptor-like ORL1 receptor, *Eur. J. Pharmacol.*, 340: 1–15, 1997;

The orphan opioid receptor and its endofenous ligand ociceptin/orphanin FQ, *Trends Pharmacol. Sci.*, 18:293–300, 1997;

Orphanin FQ is a functional anti-opioid peptide, *Neuroscience*, 75:333–337, 1996;

Orphanin FQ/nociceptin-lack of antinociceptive, hyperalgesic or allodynic effects in acute thermal or mechanical tests, following intracerebroventricular or intrathecal administration to mice or rats, *Eur. J. pain*, 2:267–280, 1998;

Orphanin FQ acts as an anxiolytic to attenuate behavioral responses to stress, *Proc. Natl. Acad. Sci., USA*, 94: 14854–14858, 1997;

Orphanin FQ, an agonist of orphan opioid receptor ORL1, stimulates feeding in rats, *Neuroreport*, 8:369–371, 1996;

Facilitation of long-term potentiation and memory in mice lacking nociceptin receptors, *Nature*, 394: 577–581, 1998;

Distribution of nociceptin/orphanin FQ receptor transcript in human central nervous system and immune cells, *J. Neuroimmuno*, 81:184–192, 1998;

Orphamin FQ plays a role in sepsis, *Prog. Clin. Biol. Res.* (1998), 397, 315–325.

Objects of the present invention are the compounds of formula I and pharmaceutically acceptable addition salts thereof, racemic mixtures and their corresponding enantiomers, the preparation of the above-mentioned compounds, medicaments containing them and their manufacture as well as the use of the above-mentioned compounds in the control or prevention of illnesses, especially of illnesses and disorders of the kind referred above, or in the manufacture of corresponding medicaments.

SUMMARY OF THE INVENTION

The present invention relates to compounds of the general formula

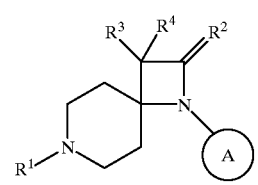

I wherein
$R^1$ is $C_{6-12}$-cycloalkyl, optionally substituted by lower alkyl or C(O)O lower alkyl, indan-1-yl or indan-2-yl, optionally substituted by lower alkyl; acenaphthen-1-yl; bicyclo[3.3.1]non-9-yl, octahydro-inden-2-yl; 2,3-dihydro-1H-phenalen-1-yl; 2,3,3a,4,5,6-hexahydro-1-H-phenalen-1-yl, decahydro-azulen-2-yl; bicyclo[6.2.0]dec-9-yl; decahydro-naphthalen-1-yl, decahydro-naphthalen-2-yl; tetrahydro-naphthalen-1-yl, tetrahydro-naphthalen-2-yl or 2-oxo-1,2-diphenylethyl;
$R^2$ is =O or hydrogen,
$R^3$ is hydrogen, isoindolyl-1,3-dione, lower alkoxy, lower alkyl, amino, benzyloxy, —$CH_2OR^5$ or —$CH_2N(R^5)_2$;
$R^4$ is hydrogen or —$CH_2OR^5$;
$R^5$ is hydrogen or lower alkyl;

is cyclohexyl or phenyl, optionally substituted by lower alkyl, halogen or alkoxy, and to pharmaceutically acceptable acid addition salts thereof.

The compounds of formula I and their salts are characterized by valuable therapeutic properties. It has surprisingly been found that the compounds of the present invention are agonists of the orphanin FQ (OFQ) receptor. Consequently they are useful in the treatment of psychiatric, neurological and physiological disorders, especially, but not limited to, amelioration of symptoms of anxiety and stress disorders, depression, trauma, memory loss due to Alzheimer's disease or other dementias, epilepsy and convulsions, acute and/or chronic pain conditions, symptoms of addictive drug withdrawal, control of water balance, Na+ excretion, arterial blood pressure disorders and metabolic disorders such as obesity.

DETAILED DESCRIPTION OF THE INVENTION

The following definitions of the general terms used in the present description apply irrespective of whether the terms in question appear alone or in combination, such as lower alkyl and lower alkoxy.

The term "lower alkyl" denotes a straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group containing from 6–12 carbon atoms, preferred are cyclohexyl, cyclooctyl, cyclononyl and cyclodecyl.

The term "halogen" denotes chlorine, iodine, fluorine and bromine.

The term "pharmaceutically acceptable acid addition salts" embraces salts with inorganic and organic acids well-known in the art for pharmaceutic purposes, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present invention are those of formula I, in which $R^1$ is $(C_{6-9})$-cycloalkyl or decahydro-naphthalen-2-yl, for example the following compounds:

3,3-bis-Hydroxymethyl-7-(cis-4-isopropyl-cyclohexyl)-1-phenyl-1,7-diaza-spiro[3.5]nonan-2-one;
7-(cis-4-Isopropyl-cyclohexyl)-1-phenyl-1,7-diaza-spiro[3.5]nonan-2-one;
7-(cis-4-Isopropyl-cyclohexyl)-1-phenyl-1,7-diaza-spiro[3.5]nonane;
7-Cyclononyl-1-phenyl-1,7-diaza-spiro[3.5]nonan-2-one;
7-Cyclononyl-1-phenyl-1,7-diaza-spiro[3.5]nonane;
7-Cyclooctyl-1-phenyl-1,7-diaza-spiro[3.5]nonan-2-one;
7-Cycloheptyl-1-phenyl-1,7-diaza-spiro[3.5]nonan-2-one; and (2RS,4aSR,8aRS)-7-(Decahydro-naphthalen-2-yl)-1-phenyl-1,7-diaza-spiro[3.5]nonan-2-one.

The present compounds of formula I and their pharmaceutically acceptable salts can be prepared by methods known in the art, for example by processes described below, which comprise:

a) reductively aminating a compound of formula

II with a compound of formula

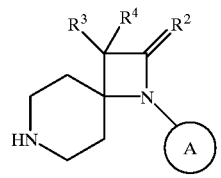

III wherein $R^1$, $R^2$ $R^3$, $R^4$ and

have the significances given above, or b) condensing an imine of formula

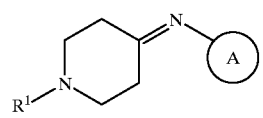

IV with a carboxylic acid derivative of formula

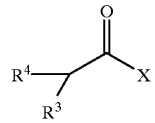

V to a compound of formula

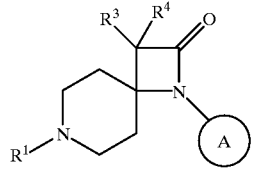

I-1 wherein $R^1$, $R^3$, $R^4$ and

have the significances given above, and X is halogen, or c) condensing a 4-phenylamino-4-piperidinocarbonitrile or a 4-cyclohexylamino-4-piperidinocarbonitrile of formula

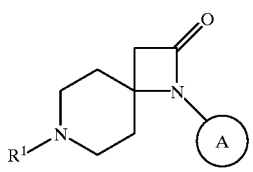

VI with methylbromoacetate in the presence of a metal to a compound of formula

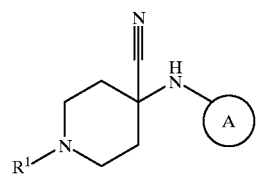

I-2 wherein R<sup>1</sup> and

are have the significances given above, or
  d) reducing a compound of formula

I-1

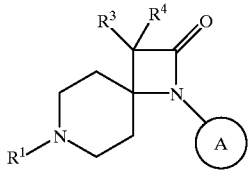

to an azetidine of formula

I-3

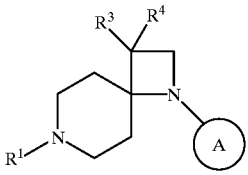

wherein R$^1$, R$^3$, R$^4$ and

have the significances given above, or
  e) hydrogenating a compound of formula I, wherein

is phenyl, to a compound of formula I, wherein

is cyclohexyl, and, if desired, converting a racemic mixture into its enantiomeric components thus obtaining optically pure compounds, and/or converting the compounds obtained into pharmaceutically acceptable acid addition salts.

In accordance with process variant a) the reductive amination of a keto compound of formula II with an amine of formula III is carried out by stirring with a dehydrating agent in the presence of molecular sieves (4Å), in an inert solvent, such as toluene or tetrahydrofuran (THF), at reflux temperature. An alternative method is the dehydration in the presence of an acidic catalyst with removal of water, e.g. with azeotropic removal of water, or with tetraisopropyl-orthotitanate in THF.

The resulting intermediate enamine or imine is then reduced with a reducing agent, such as metal hydrides or hydrogen in the presence of a hydrogenating catalyst, preferably with sodium cyanoborohydride in a protic solvent, for example in a mixture of THF and ethanol at acidic pH.

Examples of corresponding keto compounds of formula II are the following:

2-indanone, 1,3-dihydro-4-methyl-2H-inden-2-one, 4-(1-methylethyl)cyclohexanone, cis-octahydro-inden-2-one, cyclopctanone, cyclodecanone, decahydro-azulen-2-one, cyclononanone, cycloundecanone, cycloheptanone, cyclododecanone, bicyclo[6.2.0]dec-9-one or 1,3-dihydro-2H-inden-2-one.

The condensation of an imine of formula IV with a ketene of formula V in accordance with variant b) is carried out in the presence of a base, such as triethylamine. The reaction is carried out at 0° C. and then stirred at room temperature for about 24 h.

In accordance with process variant c) a 4-phenyl- or 4-cyclohexyl-4-piperidinocarbonitrile of formula VI is condensed with methylbromoacetate in the presence of a metal, such as zinc. The reaction is carried out in an inert solvent, for example THF. The mixture is heated for about 1½h, the phases are separated and isolated to yield a compound of formula I-2.

The reduction of a compound of formula I-1 to an azetidine of formula I-3 in accordance with process variant d) is carried out with a reducing agent, preferably with a metal hydride, such as lithium aluminiumhydride by methods, known in the art. A mixture of aluminium trichloride and the metal hydride is treated with a compound of formula I-1 in THF to yield a compound of formula I-3.

Process variant e) relates to the hydrogenation of a compound of formula I wherein

is phenyl. The desired cyclohexyl ring is yielded in a protic solvent, such as methanol and in the presence of a hydrogenating catalyst, for example in the presence of platinum oxide. The reaction is carried out under hydrogen pressure between 1 and 50 bar.

Racemic mixtures can be converted into their enantiomeric components in conventional manner, for example by preparative HPLC.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methanesulphonates, p-toluenesulfonates and the like are examples of such salts.

The compounds of formulae II, III, IV, V and VI which are used as starting materials are known compounds or can be prepared by methods known per se.

The following scheme 1 describes the cyclization (condensation) of compounds of formulae IV and V or II and III-1 to a compound of formula I-1. In scheme 2 is shown the cyclization (condensation) of compounds of formula VI with methylbromoacetate to compounds of formula I-1.

Scheme 1

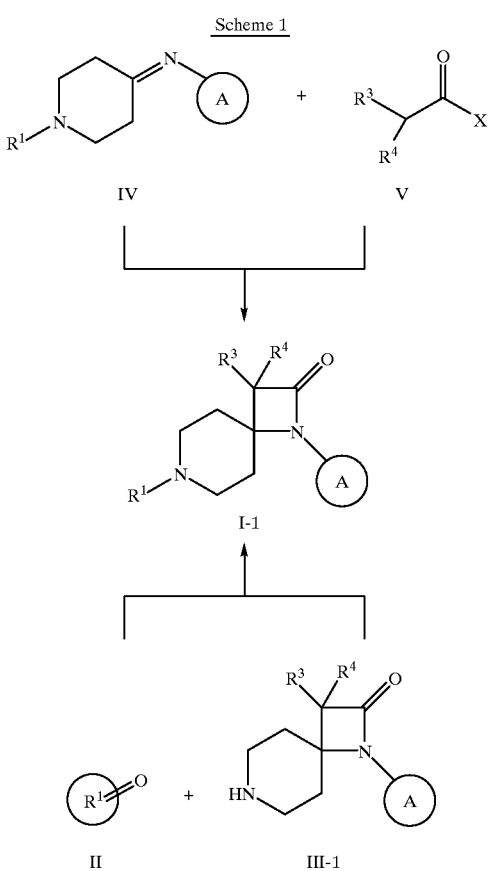

wherein R¹, R³, R⁴ and

have the significances given above, and X is halogen.

Scheme 2

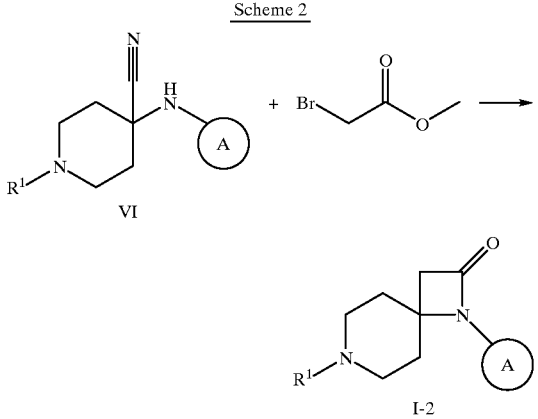

As mentioned earlier, the compounds of formula I and their pharmaceutically usuable addition salts possess valuable pharmacodynamic properties. It has been found that the compounds of the present invention are agonists of the OFQ receptor and have effects in animal models of psychiatric, neurological and physiological disorders, such as anxiety, stress disorders, depression, trauma, memory loss due to Alzheimer's disease or other dementias, epilepsy and convulsions, acute and/or chronic pain conditions, symptoms of addictive drug withdrawal, control of water balance, $Na^+$ excretion, arterial blood pressure disorders and metabolic disorders such as obesity.

The compounds were tested for pharmacologic activity in accordance with the methods given hereinafter:

Methods of OFQ-R Binding Assay

Cell Culture

HEK-293 cells adapted to suspension growth (293s) were cultured in HL medium plus 2% FBS. The cells were transfected with the rat OFQ receptor cDNA (LC132), FEBS Lett. 347, 284–288,1994, cloned in the expression vector pCEP4 (Invitrogen, SanDiego, Calif., U.S.A.) using lipofectin (Life Technologies, Bethesda, Md., U.S.A.). Transfected cells were selected in the presence of hygromycin (1000 U/ml) (Calbiochem, SanDiego, Calif., U.S.A.). A pool of resistant cells was tested for OFQ-R expression by binding of [³H]-OFQ (Amersham PLC, Buckinghamshire, England). These cells (293s-OFQ-R) were expanded for large scale culture and membrane preparation.

Membrane Preparation

293s-OFQ-R cells were harvested by centrifugation, washed 3 times with phosphate buffered saline (PBS) before resuspension in buffer A (50 mM Tris-HCl, pH 7.8, 5 mM $MgCl_2$, 1 mM EGTA) and disruption with a tissue homogenizer (30 seconds, setting 4, Pt 20, Kinematica, Kriens-Lucern, Switzerland). A total membrane fraction was obtained by centrifugation at 49,000×g at 4° C. This procedure was repeated twice and the pellet was resuspended in buffer A. Aliquots were stored at −70° C. and protein concentrations were determined using the BCA™ Protein Assay Reagent (Pierce, Rockford, Ill.) following the manufacturer's recommendations.

Binding Assays

[³H]-OFQ competition studies were carried out with 77 μg membrane protein in a final assay volume of 0.5 ml buffer A plus 0.1% BSA and 0.01% bacitracin (Boehringer-Mannheim, Mannheim, Germany) for one hour at room temperature. 50 nM unlabeled OFQ was used to define the non-specific binding. The assays were terminated by filtration through Whatman GF/C filters (Unifilter-96, Canberra Packard S.A., Zurich, Switzerland) pretreated with 0.3% polyethylenimine (Sigma, St. Louis, Mo., U.S.A.) and 0.1% BSA (Sigma) for 1 hour. The filters were washed 6 times with 1 ml of ice bold 50 mM Tris-HCl pH 7.5. The retained radioactivity was counted on a Packard Top-Count microplate scintillation counter after addition of 40 μl of Microscint 40 (Canberra Packard). The effects of compounds were determined using at least 6 concentrations in triplicate, and determined twice. $IC_{50}$ values were determined by curve fitting and these values were converted to $K_i$ values by the method of Cheng and Prusoff, Biochem. Pharmacol., 22, 3099, 1973.

The affinity to the OFQ-receptor, given as $pK_i$, is in the range of 6,5 to 9,3.

GTPγS Binding Assay

This assay was used to define whether the compounds of this invention are agonists or antagonists of the OFQ receptor.

Agonist-mediated binding of GTPγS was investigated in 96-well plates using a Scintillation Proximity Assay (SPA) using either hOFQR membranes or membranes prepared from cells transfected with the various human opiate receptors (μ, δ and κ). Binding was performed in 200 μl 20 mM HEPES-buffer (pH 7.4, plus 6 mM $MgCl_2$ and 100 mM NaCl), supplemented with 20 μM GDP, 10 μm cold GTPγS and 0.3 nM GTP[γ$^{35}$]S (1130 Ci/mmol). Twenty μg membranes, 1 mg wheatgerm agglutinin SPA beads (Amersham, Little Chalfont, UK) and either OFQ ($10^{-5}$ M to $10^{-10}$ M) or synthetic compounds ($10^{-4}$ M to $10^{-9}$ M) were added.

The reaction mixture was incubated on a shaker for 60 min at 22° C. and then centrifuged for 5 min at 1500 rpm in an Eppendorf 5403 centrifuge. Finally the plates were read in a Top counter (Packard).

Compounds of this invention have been shown to be agonists of the OFQ receptor having $PEC_{50}$ ranges from about 5.8 to about 7.3.

The preparation of the following compounds is described in Examples 1–54:

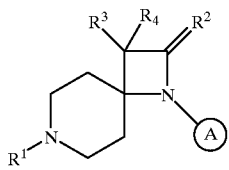

| R$^1$ | R$^2$ | R$^3$ | R$^4$ | A | Example No. |
|---|---|---|---|---|---|
| 2-indanyl | O | H | H | phenyl | 1 |
| 4-methyl-2-indanyl | O | H | H | phenyl | 2 |
| 4-isopropylcyclohexyl | O | H | H | phenyl | 3 |
| 2-indanyl | H$_2$ | H | H | phenyl | 4 |
| 4-methyl-2-indanyl | H$_2$ | H | H | phenyl | 4 |
| 4-isopropylcyclohexyl | H$_2$ | H | H | phenyl | 5 |
| 4-isopropylcyclohexyl (cis) | H$_2$ | H | H | phenyl | 6 |
| 4-isopropylcyclohexyl (cis) | O | H | H | phenyl | 7 |

-continued
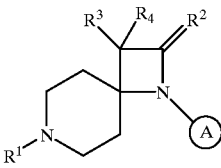
| R¹ | R² | R³ | R⁴ | A | Example No. |
|---|---|---|---|---|---|
| 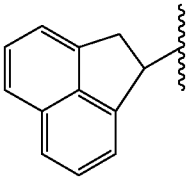 | O | H | H | phenyl | 8 |
| 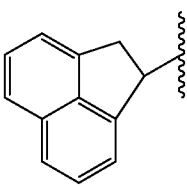 | H₂ | H | H | phenyl | 9 |
| 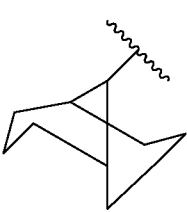 | O | H | H | phenyl | 10 |
| 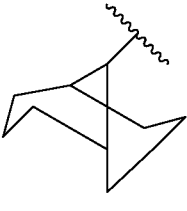 | H₂ | H | H | phenyl | 11 |
| 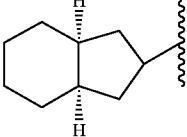 | O | H | H | phenyl | 12 |
| 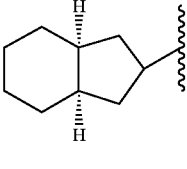 | H₂ | H | H | phenyl | 13 |
| 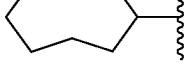 | O | H | H | phenyl | 14 |

-continued
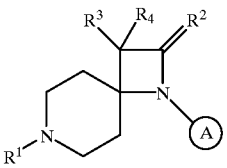
| R¹ | R² | R³ | R⁴ | A | Example No. |
|---|---|---|---|---|---|
| 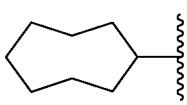 | H₂ | H | H | phenyl | 15 |
| 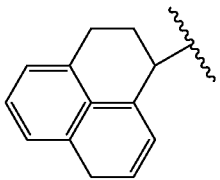 | O | H | H | phenyl | 16 |
| 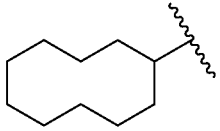 | O | H | H | phenyl | 17 |
| 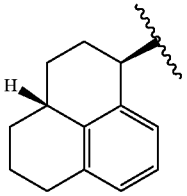 | O | H | H | phenyl | 18 |
| 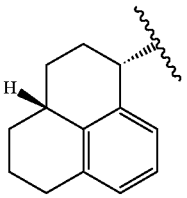 | O | H | H | phenyl | 19 |
| 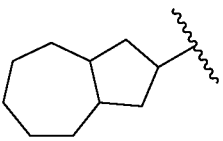 | O | H | H | phenyl | 20 |
| 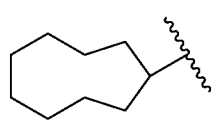 | O | H | H | phenyl | 21 |

-continued
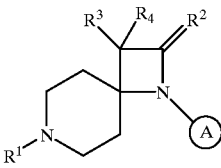
| R¹ | R² | R³ | R⁴ | A | Example No. |
|---|---|---|---|---|---|
| 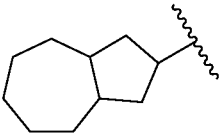 | H₂ | H | H | phenyl | 22 |
| 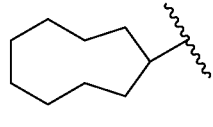 | H₂ | H | H | phenyl | 23 |
| 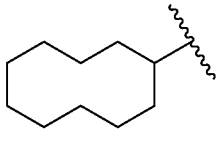 | H₂ | H | H | phenyl | 24 |
| 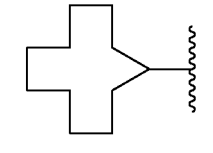 | O | H | H | phenyl | 25 |
| 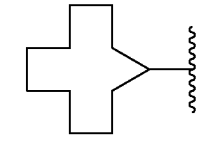 | H₂ | H | H | phenyl | 26 |
| 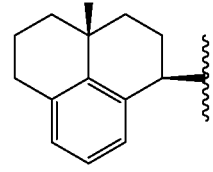 | H₂ | H | H | phenyl | 27 (1RS, 3aSR) |
| 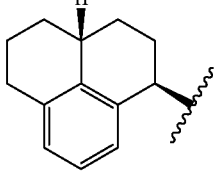 | H₂ | H | H | phenyl | 28 (1RS, 3aRS) |
| 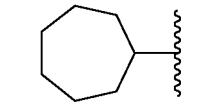 | O | H | H | phenyl | 29 |

-continued
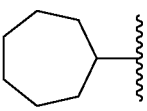
| R¹ | R² | R³ | R⁴ | A | Example No. |
|---|---|---|---|---|---|
| 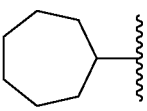 | H₂ | H | H | phenyl | 30 |
| 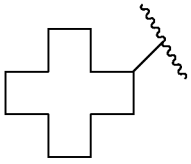 | O | H | H | phenyl | 31 |
| 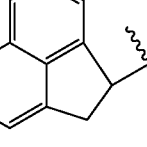 | O | H | H | 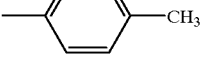 | 32 |
| 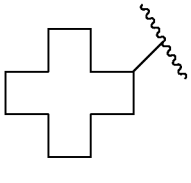 | H₂ | H | H | phenyl | 33 |
| 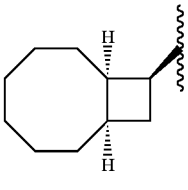 | O | H | H | phenyl | 34 |
| 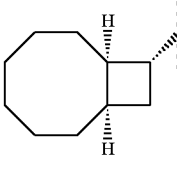 | O | H | H | phenyl | 35 |
| 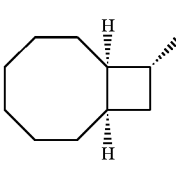 | H₂ | H | H | phenyl | 36 |

-continued
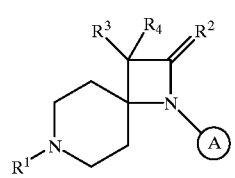
| R¹ | R² | R³ | R⁴ | A | Example No. |
|---|---|---|---|---|---|
| 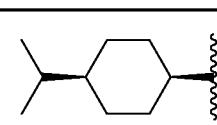 | O | 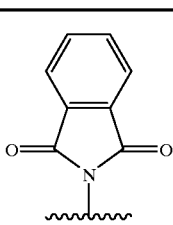 | H | phenyl | 37 |
| 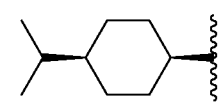 | O | —OCH₃ | H | phenyl | 38 |
| 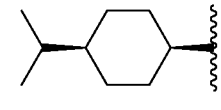 | O | 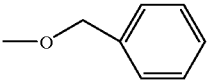 | H | phenyl | 39 |
| 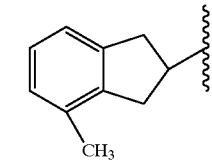 | O | —CH₂OH | —CH₂OH | phenyl | 40 |
| 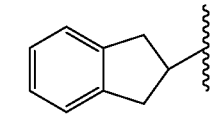 | O | —CH₂OH | —CH₂OH | phenyl | 41 |
| 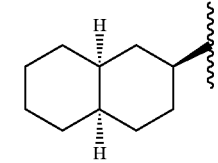 | I | H | H | phenyl | 42 |
| 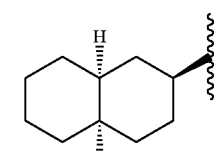 | H₂ | H | H | phenyl | 43 |
| 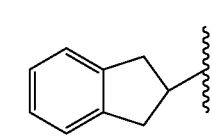 | H₂ | —CH₂OH | —CH₂OH | phenyl | 44 |

-continued
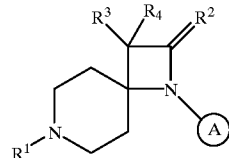
| R¹ | R² | R³ | R⁴ | A | Example No. |
|---|---|---|---|---|---|
| 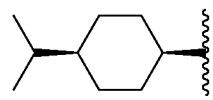 | O | —CH₂OH | —CH₂OH | phenyl | 45 |
| 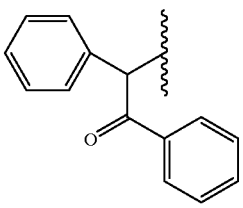 | O | H | H | phenyl | 46 |
| 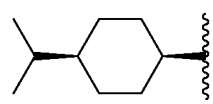 | H₂ | —CH₂OH | —CH₂OH | phenyl | 47 |
| 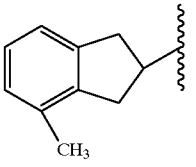 | H₂ | —CH₂OH | —CH₂OH | phenyl | 48 |
| 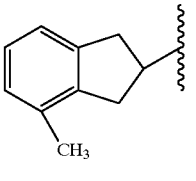 | O | H | —CH₂OH | phenyl | 49 |
| 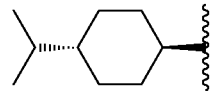 | O | H | —CH₂OH | phenyl | 50 |
| 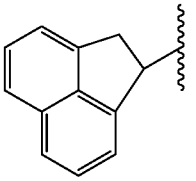 | O | H | H | 3-F-phenyl | 51 |
| 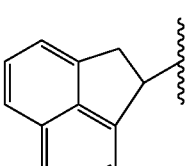 | O | H | H | 4-Cl-phenyl | 52 |

-continued

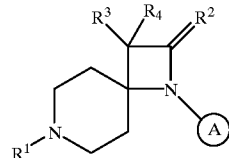

| R¹ | R² | R³ | R⁴ | A | Example No. |
|---|---|---|---|---|---|
| 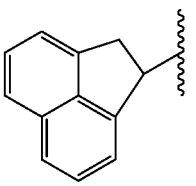 | O | H | H | 3-Cl-phenyl | 53 |
| 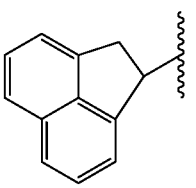 | O | H | H | 4-F-phenyl | 54 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, the effective dosage for oral or parenteral administration is 0,01–20 mg/kg/day, preferred as a dosage of 0,1–10 mg/kg/day for all described indications. The daily dosage for an adult of 70 kg weight is therefore between 0,7–1400 mg/day, preferred is 7–700 mg/day, although the above upper limit can also be exceeded when necessary.

The following Examples illustrate the present invention without limiting it. All temperatures are given in degrees Celsius.

EXAMPLE 1

7-Indan-2-yl-1-phenyl-1,7-diaza-spiro[3.5]nonan-2-one hydrochloride (1:1)

2-Indanone (2.3 mmol) was dissolved in toluene, 1-phenyl-1,7-diaza-spiro[3.5]nonan-2-one (2.3 mmol) and molecular sieves (4 Å, 2.5 g) were added. The mixture was refluxed with stirring for 16 h, filtered and the filtrate was evaporated. The residue was dissolved in THF/ethanol (25 ml, 9:1), sodium cyanoborohydride (2.3 mmol) was added and the pH was adjusted to 4. The mixture was stirred for 3 h at room temperature. Ice-water (30 ml) and potassium carbonate solution (50%, 30 ml) were added. The mixture was extracted twice with methylene chloride, organic phases were pooled, dried with MgSO4 and concentrated. Chromatography on silica gel (ethyl acetate/n-hexane, 1:1) yielded the desired product which was crystallized as its HCl-salt from ethanol/ethyl acetate. 0.47 g (55%) 7-indan-2-yl-1-phenyl-1,7-diaza-spiro[3.5]nonan-2-one hydrochloride (1:1) as a colorless solid, m.p.>250° C. and MS: m/e=332.5 (M⁺).

EXAMPLE 2

(RS)-7-(4-Methyl-indan-2-yl)-1-phenyl-1,7-diaza-spiro[3.5]nonan-2-one hydrochloride (1:1)

The title compound, m.p.>250° C. and MS: m/e=347.4 (M+H⁺) was prepared in accordance with the general method of example 1 from 1,3-dihydro-4-methyl-2H-inden-2-one and 1-phenyl-1,7-diaza-spiro[3.5]nonan-2-one.

EXAMPLE 3 cis-7-(4-Isopropyl-cyclohexyl)-1-phenyl-1,7-diaza-spiro [3.5]nonan-2-one hydrochloride (1:1)

The title compound, m.p.>250° C. and MS: m/e=341.3 (M+H$^+$) was prepared in accordance with the general method of example 1 from 4-(1-methylethyl)-cyclohexanone and 1-phenyl-1,7-diaza-spiro[3.5]nonan-2-one.

EXAMPLE 4

(RS)-7-(4-Methyl-indan-2-yl)-1-phenyl-1,7-diaza-spiro [3.5]nonane hydrochloride (1:1)

A mixture of aluminiumtrichloride (3 mmol) and lithium aluminiumhydride (3 mmol) in diethylether (5 ml) was heated for 1 h. The solution was then added to a mixture of (RS)-7-(4-methyl-indan-2-yl)-1-phenyl-1,7-diaza-spiro[3.5] nonan-2-one(1 mmol) in THF (20 ml). Heating commenced for 4 h. Water (50 ml) and methylenchloride (100 ml) were added, the phases were separated and the organic phase was dried with Na$_2$SO$_4$ and concentrated to yield the desired product which was crystallized as its HCl-salt from ethanol/ethyl acetate. 80 mg (20%) (RS)-7-(4-methyl-indan-2-yl)-1-phenyl-1,7-diaza-spiro[3.5]nonane hydrochloride (1:1) as a colorless solid, >219° C. dec. and MS: m/e=333.3 (M+H$^+$).

EXAMPLE 5 cis-7-(4-Isopropyl-cyclohexyl)-1-phenyl-1,7-diaza-spiro [3.5]nonane hydrochloride (1:1)

The title compound, m.p. 207° C. and MS: m/e=327.4 (M+H$^+$) was prepared in accordance with the general method of example 4 from cis-7-(4-isopropyl-cyclohexyl)-1-phenyl-1,7-diaza-spiro[3.5]nonan-2-one.

EXAMPLE 6 trans-7-(4-Isopropyl-cyclohexyl)-1-phenyl-1,7-diaza-spiro [3.5]nonane hydrochloride (1:1)

The title compound, m.p. 229° C. and MS: m/e=327.4 (M+H$^+$) was prepared in accordance with the general method of example 4 from trans-7-(4-isopropyl-cyclohexyl)-1-phenyl-1,7-diaza-spiro[3.5]nonan-2-one.

EXAMPLE 7 trans-7-(4-Isopropyl-cyclohexyl)-1-phenyl-1,7-diaza-spiro [3.5]nonan-2-one hydrochloride (1:1)

The title compound, m.p.>250° C. and MS: m/e=341.3 (M+H$^+$) was prepared in accordance with the general method of example 1 from 4-(1-methylethyl)-cyclohexanone and 1-phenyl-1,7-diaza-spiro[3.5]nonan-2-one.

EXAMPLE 8

(RS)-7-Acenaphthen-1-yl-1-phenyl-1,7-diaza-spiro[3.5] nonan-2-one hydrochloride (1:1)

The title compound, white solid, m.p. 245° C. (dec.) and MS: m/e=369.3 (M+H$^+$) was prepared in accordance with the general method of example aa from (RS)-4-phenylamino-1-(acenaphthen-1-yl)-piperidine-4-carbonitrile.

EXAMPLE 9

(RS)-7-Acenaphthen-1-yl-1-phenyl-1,7-diaza-spiro[3.5] nonane hydrochloride (1:1)

The title compound, white solid, m.p. 184° C. (dec.) and MS: m/e=355.3 (M+H$^+$) was prepared in accordance with the general method of example 4 from (RS)-7-acenaphthen-1-yl-1-phenyl-1,7-diaza-spiro[3.5]nonan-2-one.

EXAMPLE 10

7-Bicyclo[3.3.1]non-9-yl-1-phenyl-1,7-diaza-spiro[3.5] nonan-2-one hydrochloride (1:1)

The title compound, white solid, m.p. 292° C. and MS: m/e=339.3 (M+H$^+$) was prepared in accordance with the general method of example aa from 1-bicyclo[3.3.1]non-9-yl-4-phenylamino-piperidine-4-carbonitrile.

EXAMPLE 11

7-Bicyclo[3.3.1]non-9-yl-1-phenyl-1,7-diaza-spiro[3.5] nonane hydrochloride (1:1)

The title compound, white solid, m.p. 178° C. and MS: m/e=325.4 (M+H$^+$) was prepared in accordance with the general method of example 4 from 7-bicyclo[3.3.1]non-9-yl-1-phenyl-1,7-diaza-spiro[3.5]nonan-2-one.

EXAMPLE 12

RS)-7-(Octahydro-inden-2-yl)-1-phenyl-1,7-diaza-spiro [3.5]nonan-2-one hydrochloride (1:1)

The title compound, m.p. 312° C. (dec.) and MS: m/e= 339.3 (M+H$^+$) was prepared in accordance with the general method of example 1 from cis-octahydro-inden-2-one and 1-phenyl-1,7-diaza-spiro[3.5]nonan-2-one.

EXAMPLE 13

(RS)-7-(Octahydro-inden-2-yl)-1-phenyl-1,7-diaza-spiro [3.5]nonane hydrochloride (1:1)

The title compound, white solid, m.p. 184° C. (dec.) and MS: m/e=325.4 (M+H$^+$) was prepared in accordance with the general method of example 4 from (RS)-7-(octahydro-inden-2-yl)-1-phenyl-1,7-diaza-spiro[3.5]nonan-2-one.

EXAMPLE 14

7-Cyclooctyl-1-phenyl-1,7-diaza-spiro[3.5]nonan-2-one hydrochloride (1:1)

The title compound, m.p. 294° C. (dec.) and MS: m/e= 327.3 (M+H$^+$) was prepared in accordance with the general method of example 1 from cyclooctanone and 1-phenyl-1, 7-diaza-spiro[3.5]nonan-2-one.

EXAMPLE 15

7-Cyclooctyl-1-phenyl-1,7-diaza-spiro[3.5]nonane hydrochloride (1:1)

The title compound, white solid, m.p. 186° C. (dec.) and MS: m/e=313.3 (M+H$^+$) was prepared in accordance with the general method of example 4 from 7-cyclooctyl-1-phenyl-1,7-diaza-spiro[3.5]nonan-2-one.

EXAMPLE 16

(RS)-7-(2,3-Dihydro-1H-phenalen-1-yl)-1-phenyl-1,7-diaza-spiro[3.5]nonan-2-one hydrochloride (1:1)

The title compound, pale brown solid, m.p. 203° C. (dec.) and MS: m/e=383.2 (M+H$^+$) was prepared in accordance with the general method of example aa from (RS)-7-(2,3-dihydro-1H -phenalen-1-yl)-piperidine-4-carbonitrile.

EXAMPLE 17

7-Cyclodecyl-1-phenyl-1,7-diaza-spiro[3.5]nonan-2-one hydrochloride (1:1)

The title compound, m.p. 260° C. (dec.) and MS: m/e= 355.4 (M+H$^+$) was prepared in accordance with the general method of example 1 from cyclodecanone and 1-phenyl-1, 7-diaza-spiro[3.5]nonan-2-one.

EXAMPLE 18
(1RS,3aRS)-7-(2,3,3a,4,5,6-Hexahydro-1H-phenalen-1-yl)-1-phenyl-1,7-diaza-spiro[3.5]nonan-2-one hydrochloride (1:1)

The title compound, white solid, m.p. 232° C. (dec.) and MS: m/e=387.3 (M+H$^+$) was prepared in accordance with the general method of example aa from(1RS,3aRS)-7-(2,3,3a,4,5,6-hexahydro-1H-phenalen-1-yl)-piperidine-4-carbonitrile.

EXAMPLE 19
(1RS,3aSR)-7-(2,3,3a,4,5,6-Hexahydro-1H-phenalen-1-yl)-1-phenyl-1,7-diaza-spiro[3.5]nonan-2-one hydrochloride (1:1)

The title compound, white solid, m.p. 162° C. and MS: m/e=387.3 (M+H$^+$) was prepared in accordance with the general method of example aa from (1RS,3aSR)-7-(2,3,3a,4,5,6-hexahydro-1H-phenalen-1-yl)-piperidine-4-carbonitrile.

EXAMPLE 20
7-(Decahydro-azulen-2-yl)-1-phenyl-1,7-diaza-spiro[3.5]nonan-2-one hydrochloride (1:1) (mixture of diastereoisomers)

The title compound, white solid, m.p. 334° C. (dec.) and MS: m/e=353.4 (M+H$^+$) was prepared in accordance with the general method of example 1 from decahydro-azulen-2-one and 1-phenyl-1,7-diaza-spiro[3.5]nonan-2-one.

EXAMPLE 21
7-Cyclononyl-1-phenyl-1,7-diaza-spiro[3.5]nonan-2-one hydrochloride (1:1)

The title compound, white solid, m.p. 249° C. (dec.) and MS: m/e=341.3 (M+H$^+$) was prepared in accordance with the general method of example 1 from cyclononanone and 1-phenyl-1,7-diaza-spiro[3.5]nonan-2-one.

EXAMPLE 22
7-(Decahydro-azulen-2-yl)-1-phenyl-1,7-diaza-spiro[3.5]nonane hydrochloride (1:1) (mixture of diastereoisomers)

The title compound, white solid, m.p. 212° C. (dec.) and MS: m/e=369.3 (M+H$^+$) was prepared in accordance with the general method of example 4 from 7-(decahydro-azulen-2-yl)-1-phenyl-1,7-diaza-spiro[3.5]nonan-2-one (mixture of diastereoisomers).

EXAMPLE 23
7-Cyclononyl-1-phenyl-1,7-diaza-spiro[3.5]nonane fumarate (1:2.25)

Reduction of 7-cyclononyl-1-phenyl-1,7-diaza-spiro[3.5]nonan-2-one in accordance with the general method of example 4 and treatment of the base with fumaric acid in diethyl ether yielded the title compound, white solid, m.p. 138° C. (dec.) and MS: m/e=327.4 (M+H$^+$).

EXAMPLE 24
7-Cyclodecyl-1-phenyl-1,7-diaza-spiro[3.5]nonane fumarate (1:3.1)

Reduction of 7-cyclodecyl-1-phenyl-1,7-diaza-spiro[3.5]nonan-2-one in accordance with the general method of example 4 and treatment of the base with fumaric acid in diethyl ether yielded the title compound, white solid, m.p. 141° C. (dec.) and MS: m/e=341.3 (M+H$^+$).

EXAMPLE 25
7-Cycloundecyl-1-phenyl-1,7-diaza-spiro[3.5]nonan-2-one hydrochloride (1:1)

The title compound, white solid, m.p. 279° C. and MS: m/e=369.4 (M+H$^+$) was prepared in accordance with the general method of example 1 from cycloundecanone and 1-phenyl-1,7-diaza-spiro[3.5]nonan-2-one.

EXAMPLE 26
7-Cycloundecyl-1-phenyl-1,7-diaza-spiro[3.5]nonane; fumarate (1:0.78)

Reduction of 7-cycloundecyl-1-phenyl-1,7-diaza-spiro[3.5]nonan-2-one in accordance with the general method of example 4 and treatment of the base with fumaric acid in diethyl ether yielded the title compound, white solid, m.p. 174° C. (dec.) and MS: m/e=355.4 (M+H$^+$).

EXAMPLE 27
(1RS,3aSR)-7-(2,3,3a,4,5,6-Hexahydro-1H-phenalen-1-yl)-1-phenyl-1,7-diaza-spiro[3.5]nonane fumarate (1:1)

Reduction of (1RS,3aSR)-7-(2,3,3a,4,5,6-hexahydro-1H-phenalen-1-yl)-1-phenyl-1,7-diaza-spiro[3.5]nonan-2-one in accordance with the general method of example 4 and treatment of the base with fumaric acid in diethyl ether yielded the title compound, white solid, m.p. 136° C. and MS: m/e=373.4 (M+H$^+$).

EXAMPLE 28
(1RS,3aRS)-7-(2,3,3a,4,5,6-Hexahydro-1H-phenalen-1-yl)-1-phenyl-1,7-diaza-spiro[3.5]nonane fumarate (1:1)

Reduction of (1RS,3aRS)-7-(2,3,3a,4,5,6-hexahydro-1H-phenalen-1-yl)-1-phenyl-1,7-diaza-spiro[3.5]nonan-2-one in accordance with the general method of example 4 and treatment of the base with fumaric acid in diethyl ether yielded the title compound, white solid, m.p. 175° C. and MS: m/e=373.4 (M+H$^+$).

EXAMPLE 29
7-Cycloheptyl-1-phenyl-1,7-diaza-spiro[3.5]nonan-2-one hydrochloride (1:1)

The title compound, white solid, m.p. 289° C. (dec.) and MS: m/e=313.2 (M+H$^+$) was prepared in accordance with the general method of example 1 from cycloheptanone and 1-phenyl-1,7-diaza-spiro[3.5]nonan-2-one.

EXAMPLE 30
7-Cycloheptyl-1-phenyl-1,7-diaza-spiro[3.5]nonane fumarate (1:1)

Reduction of 7-cycloheptyl-1-phenyl-1,7-diaza-spiro[3.5]nonan-2-one in accordance with the general method of example 4 and treatment of the base with fumaric acid in diethyl ether yielded the title compound, white solid, m.p. 190° C. (dec.) and MS: m/e=299.4 (M+H$^+$).

EXAMPLE 31
7-Cyclododecyl-1-phenyl-1,7-diaza-spiro[3.5]nonan-2-one hydrochloride (1:1)

The title compound, white solid, m.p. 279° C. (dec.) and MS: m/e=383.3 (M+H$^+$) was prepared in accordance with the general method of example 1 from cyclododecanone and 1-phenyl-1,7-diaza-spiro[3.5]nonan-2-one.

EXAMPLE 32
(RS)-7-Acenaphthen-1-yl-1-p-tolyl-1,7-diaza-spiro[3.5]nonan-2-one fumarate (1:1)

Reaction of (RS)-4-(p-tolylamino)-1-(acenaphthen-1-yl)-piperidine-4-carbonitrile in accordance with the general method of example aa and treatment of the base with fumaric acid in diethyl ether yielded the title compound, white solid, m.p. 209° C. and MS: m/e=383.3 (M+H$^+$).

EXAMPLE 33

7-Cyclododecyl-1-phenyl-1,7-diaza-spiro[3.5]nonane fumarate (1:1)

Reduction of 7-cyclododecyl-1-phenyl-1,7-diaza-spiro[3.5]nonan-2-one in accordance with the general method of example 4 and treatment of the base with fumaric acid in diethyl ether yielded the title compound, white solid, m.p. 179° C. and MS: m/e=369.4 (M+H$^+$).

EXAMPLE 34

(1RS,8RS,9SR)-7-Bicyclo[6.2.0]dec-9-yl-1-phenyl-1,7-diaza-spiro[3.5]nonan-2-one fumarate (1:1.5)

Reaction of (1RS,8RS)-bicyclo[6.2.0]dec-9-one and 1-phenyl-1,7-diaza-spiro[3.5]nonan-2 -one in accordance with the general method of example 1 and treatment of the base with fumaric acid in diethyl ether yielded the title compound, white solid, m.p. 203° C. and MS: m/e=353.4 (M+H$^+$).

EXAMPLE 35

(1RS,8RS,9RS)-7-Bicyclo[6.2.0]dec-9-yl-1-phenyl-1,7-diaza-spiro[3.5]nonan-2-one fumarate (1:1.3)

Reaction of (1RS,8RS)-bicyclo[6.2.0]dec-9-one and 1-phenyl-1,7-diaza-spiro[3.5]nonan-2-one in accordance with the general method of example 1 and treatment of the base with fumaric acid in diethyl ether yielded the title compound, pale brown solid, m.p. 158° C. and MS: m/e=353.4 (M+H$^+$).

EXAMPLE 36

(1RS,8RS,9RS)-7-Bicyclo[6.2.0]dec-9-yl-1-phenyl-1,7-diaza-spiro[3.5]nonane fumarate (1:1)

Reduction of (1RS,8RS,9RS)-7-Bicyclo[6.2.0]dec-9-yl-1-phenyl-1,7-diaza-spiro[3.5]nonan-2-one in accordance with the general method of example 4 and treatment of the base with fumaric acid in diethyl ether yielded the title compound, white solid, m.p. 144° C. and MS: m/e=339.4 (M+H$^+$).

EXAMPLE 37

(3RS)-2-[7-(cis-4-Isopropyl-cyclohexyl)-2-oxo-1-phenyl-1,7-diaza-spiro[3.5]non-3-yl]isoindole-1,3-dione fumarate (1:1)

cis-[1-(4-Isopropyl-cyclohexyl)-piperidin-4-ylidene]phenyl-amine (1.00 g, 3.35 mmol) and triethylamine (678 mg, 6.70 mmol) were dissolved in 50 ml diethylether and 1,3-dihydro-1,3-dioxo-2H-isoindole-2-acetyl chloride (1.5 g, 6.7 mmol) in 10 ml tetrahydrofuran were added at 0° C. The reaction mixture was stirred at room temperature for 24 h. Triethylammonium chloride was filtered off, the filtrate was washed with water, dried with MgSO$_4$ and concentrated. Chromatography on silica gel (hexane/ethyl acetate/triethylamine 40:10:1) gave 551 mg (34%) of the desired product which was precipitated as its fumarate salt from ether, m.p. 208° C., MS: m/e=486.3 (M+H$^+$).

EXAMPLE 38

(3RS)-7-(cis-4-Isopropyl-cyclohexyl)-3-methoxy-1-phenyl-1,7-diaza-spiro[3.5]nonan-2-one fumarate (1:1)

The title compound, m.p. 148° C. and MS: m/e=371.3 (M+H$^+$) was prepared in accordance with the general method of example 37 from cis-[1-(4-isopropyl-cyclohexyl)-piperidin-4-ylidene]phenyl-amine and methoxy acetyl chloride.

EXAMPLE 39

(3RS)-3-Benzyloxy-7-(cis-4-isopropyl-cyclohexyl)-1-phenyl-1,7-diaza-spiro[3.5]nonan-2-one fumarate (1:1)

The title compound, m.p.138° C. and MS: m/e=447.3 (M+H$^+$) was prepared in accordance with the general method of example 37 from cis-[1-(4-isopropyl-cyclohexyl)-piperidin-4-ylidene]phenyl-amine and benzyloxy acetyl chloride.

EXAMPLE 40

(RS)-3,3-Bis-hydroxymethyl-7-(4-methyl-indan-2-yl)-1-phenyl-1,7-diaza-spiro[3.5]nonan-2-one hydrochloride (1:1)

The title compound, m.p.>250° C. and MS: m/e=407.4 (M+H$^+$) was prepared in accordance with the general method of example 1 from 1,3-dihydro-4-methyl-2H-inden-2-one and 3,3-bis-hydroxymethyl-1-phenyl-1,7-diaza-spiro[3.5]nonan-2-one.

EXAMPLE 41

3,3-Bis-hydroxymethyl-7-indan-2-yl-1-phenyl-1,7-diaza-spiro[3.5]nonan-2-one hydrochloride (1:1)

The title compound, m.p.>250° C. and MS: m/e=393.3 (M+H$^+$) was prepared in accordance with the general method of example 1 from 1,3-dihydro-2H-inden-2-one and 3,3-bis-hydroxymethyl-1-phenyl-1,7-diaza-spiro[3.5]nonan-2-one.

EXAMPLE 42

(2RS,4aSR,8aRS)-7-(Decahydro-naphthalen-2-yl)-1-phenyl-1,7-diaza-spiro[3.5]nonan-2-one hydrochloride (1:1)

The title compound, m.p.>250° C. and MS: m/e=353.3 (M+H$^+$) was prepared in accordance with the general method of example aa from (2RS,4aSR,8aRS)-1-(decahydro-naphthalen-2-yl)-4-phenylamino-piperidine-4-carbonitrile, which was made from (2RS,4aSR,8aRS)-decahydro-naphthalen-2-ylamine in accordance with the general methods of examples ac and ad respectively.

EXAMPLE 43

(2RS,4aSR,8aRS)-7-(Decahydro-naphthalen-2-yl)-1-phenyl-1,7-diaza-spiro[3.5]nonan hydrochloride (1:1)

The title compound, m.p. 195–196° C. and MS: m/e=339.4 (M+H$^+$) was prepared in accordance with the general method of example 4 from (2RS,4aSR,8aRS)-7-(decahydro-naphthalen-2-yl)-1-phenyl-1,7-diaza-spiro[3.5]nonan-2-one.

EXAMPLE 44

(3-Hydroxymethyl-7-indan-2-yl-1-phenyl-1,7-diaza-spiro[3.5]non-3-yl)-methanol hydrochloride (1:1)

3,3-Bis-hydroxymethyl-7-indan-2-yl-1-phenyl-1,7-diazaspiro[3.5]nonan-2-one, obtained in example 41, (110 mg, 0.28 mmol) dissolved in diethylether (6 ml) and tetrahydrofurane (8 ml) was added at room temperature to a mixture of lithium aluminiumhydride (55 mg) and aluminium trichloride (190 mg) in diethylether (20 ml). The mixture was boiled for 1 h with stirring, cooled and quenched with water (7 ml). Extraction with dichloromethane, drying with Na$_2$SO$_4$ and evaporation of solvents yielded 55 mg (52%) of the title compound which was crystallized as its HCl salt from ethylacetate, m.p.>140° C. dec., MS: m/e=379.4 (M+H$^+$).

EXAMPLE 45

3,3-Bis-hydroxymethyl-7-(cis-4-isopropyl-cyclohexyl)-1-phenyl-1,7-diaza-spiro[3.5]nonan-2-one hydrochloride (1:1)

The title compound, m.p.>245° C. dec. and MS: m/e=401.5 (M+H$^+$) was prepared in accordance with the general method of example 1 from 4-isopropyl-cyclohexanone and 3,3-bis-hydroxymethyl-1-phenyl-1,7-diazaspiro[3.5]nonan-2-one and separated from the transstereoisomer by chromatography on silica gel with dichloromethane/methanol 6%.

EXAMPLE 46

(RS)-7-(2-Oxo-1,2-diphenyl-ethyl)-1-phenyl-1,7-diaza-spiro[3.5]nonan-2-one

A suspension of 2-chloro-1,2-diphenyl-ethanone (0.23 g, 1 mmol), 1-phenyl-1,7-diazaspiro[3.5]nonan-2-one (0.2 g, 0.9 mmol) and sodium bicarbonate (0.23 g) in 2-butanone was boiled for 4 h with stirring. The mixture was cooled, the solvent was removed in vacuo and the residue was purified by chromatography on silica gel with ethylacetate/hexane (1:2) to yield 0.33 g (87%) of the title compound. MS: m/e=411.3 (M+H$^+$).

EXAMPLE 47

Mixture of [3-hydroxymethyl-7-(cis- and -(trans-4-isopropyl-cyclohexyl)-1-phenyl-1,7-diaza-spiro[3.5]non-3-yl]-methanol hydrochloride (1:1)

The title compound, m.p.>126° C. dec. and MS: m/e=387.3 (M+H$^+$) was prepared in accordance with the general method of example 44 from 3,3-bis-hydroxymethyl-7-(4-isopropyl-cyclohexyl)-1-phenyl-1,7-diaza-spiro[3.5]nonan-2-one.

EXAMPLE 48

(RS)-[3-Hydroxymethyl-7-(4-methyl-indan-2-yl)-1-phenyl-1,7-diaza-spiro[3.5]non-3-yl]-methanol hydrochloride (1:1)

The title compound, m.p.>154° C. dec. and MS: m/e=393.3 (M+H$^+$) was prepared in accordance with the general method of example 44 from 3,3-bis-hydroxymethyl-7-(4-methyl-indan-2-yl)-1-phenyl-1,7-diaza-spiro[3.5]nonan-2-one.

EXAMPLE 49

Mixture of (RS)- and (SR)-3-hydroxymethyl-7-[(RS)-4-methyl-indan-2-yl]-1-phenyl-1,7-diaza-spiro[3.5]nonan-2-one hydrochloride (1:1)

The title compound, m.p.>250° C. dec. and MS: m/e=377.3 (M+H$^+$) was prepared in accordance with the general method of example 1 from 4-methyl-indan-2-one and 3-hydroxymethyl-1-phenyl-1,7-diaza-spiro[3.5]nonan-2-one.

EXAMPLE 50

(RS)-3-Hydroxymethyl-7-(trans-4-isopropyl-cyclohexyl)-1-phenyl-1,7-diaza-spiro[3.5]nonan-2-one hydrochloride (1:1)

The title compound, m.p. 218–222° C. and MS: m/e=371.3 (M+H$^+$) was prepared in accordance with the general method of example 1 from 4-isopropyl-cyclohexanone and 3-hydroxymethyl-1-phenyl-1,7-diaza-spiro[3.5]nonan-2-one and separated from the cis-stereoisomer by chromatography on silica gel with dichloromethane/methanol 2%.

EXAMPLE 51

(RS)-7-Acenaphthen-1-yl-1-(3-fluoro-phenyl)-1,7-diaza-spiro[3.5]nonan-2-one fumarate (1:1)

Reaction of (RS)-4-(3-fluoro-phenylamino)-1-(acenaphthen-1-yl)-piperidine-4-carbonitrile in accordance with the general method of example 1 and treatment of the base with fumaric acid in diethyl ether yielded the title compound, white solid, m.p. 230° C. and MS: m/e=387.3 (M+H$^+$).

EXAMPLE 52

(RS)-7-Acenaphthen-1-yl-1-(4-chloro-phenyl)-1,7-diaza-spiro[3.5]nonan-2-one fumarate (1:0.75)

Reaction of (RS)-4-(4-chloro-phenylamino)-1-(acenaphthen-1-yl)-piperidine-4-carbonitrile in accordance with the general method of example 1 and treatment of the base with fumaric acid in diethyl ether yielded the title compound, pale brown solid, m.p. 196° C. and MS: m/e=403.3 (M+H$^+$).

EXAMPLE 53

(RS)-7-Acenaphthen-1-yl-1-(3-chloro-phenyl)-1,7-diaza-spiro[3.5]nonan-2-one fumarate (1:1)

Reaction of (RS)-4-(3-chloro-phenylamino)-1-(acenaphthen-1-yl)-piperidine-4-carbonitrile in accordance with the general method of example 1 and treatment of the base with fumaric acid in diethyl ether yielded the title compound, white solid, m.p. 214° C. and MS: m/e=403.4 (M+H$^+$).

EXAMPLE 54

(RS)-7-Acenaphthen-1-yl-1-(4-fluoro-phenyl)-1,7-diaza-spiro[3.5]nonan-2-one fumarate (1:1)

Reaction of (RS)-4-(4-fluoro-phenylamino)-1-(acenaphthen-1-yl)-piperidine-4-carbonitrile in accordance with the general method of example 1 and treatment of the base with fumaric acid in diethyl ether yielded the title compound, white solid, m.p. 210° C. and MS: m/e=387.2 (M+H$^+$).

Syntheses of Intermediates

EXAMPLE aa

7-Benzyl-1-phenyl-1,7-diaza-spiro[3.5]nonan-2-one hydrochloride (1:1)

Methyl bromoacetate (136 mmol) was added dropwise to a refluxing suspension of 4-(phenylamino)-1-(phenylmethyl)-4-piperidinecarbonitrile (34 mmol) and zinc (170 mmol). The mixture was heated for 1½h after addition was complete, cooled and potassium carbonate solution (50%, 45 ml) was added. The two-phase mixture was filtered through Celite®, the phases were separated and the water phase extracted with THF. Organic phases were pooled, dried with MgSO$_4$ and concentrated. Filtration through silica gel (methylenchloride/methanol, 98:2) yielded the desired product (9.1 g, 87%) which was crystallized as its HCl-salt from ethyl acetate/ethanol. 7-Benzyl-1-phenyl-1,7-diaza-spiro[3.5]nonan-2-one hydrochloride (1:1) was isolated as a colorless solid, m.p.>250° C. and MS: m/e=307.2 (M+H$^+$).

EXAMPLE ab

1-Phenyl-1,7-diaza-spiro[3.5]nonan-2-one hydrochloride (1:1)

7-Benzyl-1-phenyl-1,7-diaza-spiro[3.5]nonan-2-one (17 mmol) was dissolved in methanol (300 ml). Palladium on carbon (10%, 0.3 g) was added and the mixture was hydrogenated at room temperature and normal pressure. Filtration and evaporation yielded the desired product which was crystallized as its HCl-salt from ethyl acetate/ethanol. 3.5 g (81%) 1-phenyl-1,7-diaza-spiro[3.5]nonan-2-one hydrochloride (1:1) as a colorless solid, m.p.>250° C. and MS: m/e=216 (M$^+$).

EXAMPLE ac
1-Bicyclo[3.3.1]non-9-yl-piperidin-4-one

1-Bicyclo[3.3.1]non-9-ylamine (2.26 g, 16.2 mmol) was dissolved in ethanol (40 ml). Potassium carbonate (224 mg, 1.62 mmol) and 1-ethyl-1-methyl-4-oxo-piperidinium iodide (6 g, 22.4 mmol) dissolved in water (15 ml) were added and the mixture was refluxed for 75 min. Water (100 ml) was added, ethanol was removed in vacuo and the residue was extracted with ethyl acetate (2×100 ml). The combined organic phases were washed with brine (100 ml), dried ($MgSO_4$) and evaporated. Column chromatography on silica gel (toluene/ethyl acetate 4:1) yielded the desired product (2.99 g, 83%) as a pale yellow oil, MS: m/e=221 ($M^+$).

EXAMPLE ad
1-Bicyclo[3.3.1]non-9-yl-4-phenylamino-piperidine-4-carbonitrile

1-Bicyclo[3.3.1]non-9-yl-piperidin-4-one (2.99 g, 13.5 mmol) was dissolved in acetic acid (15 ml). Aniline (1.36 ml, 14.9 mmol) and trimethylsilylcyanide (1.44 ml, 13.5 mmol) were added at 0° C. and the mixture was stirred for 17 h at room temperature. The reaction mixture was poured into cold ammonia solution (water/28% ammonia, 30 ml/50 ml) and extracted with dichloromethane (2×100 ml). The combined organic phases were washed with brine (100 ml), dried ($MgSO_4$) and concentrated. Column chromatography on silica gel (toluene/ethyl acetate 4:1) yielded the desired product (3.18 g, 73%) as a pale yellow solid, m.p. 168° C., MS: m/e=324.4 ($M+H^+$).

EXAMPLE ae
cis-[1-(4-Isopropyl-cyclohexyl)-piperidin-4-ylidene]phenyl-amine cis-1-(4-Isopropyl-cyclohexyl)-piperidine-4-on (5.0 g, 23.4 mmol), pyridine (3.3 g, 35.3 mmol) and molecular sieves (20 g, 4 Å) were stirred in 100 ml pentane at room temperature for 6 days. The molecular sieves were filtered off and the solvent was evaporated. The crude product was used without any further purification for the following steps.

EXAMPLE af
7-Benzyl-3,3-bis-hydroxymethyl-1-phenyl-1,7-diaza-spiro[3.5]nonan-2-one hydrochloride (1:1)

A solution of 7-benzyl-1-phenyl-1,7-diaza-spiro[3.5]nonan-2-one (0.7 mmol) in THF (4 ml) was added to a solution of lithiumdiisopropylamide (2 mmol) and N,N,N'N'-tetramethylethylendiamine (2 mmol) in THF (5 ml) at −75° C. The mixture was stirred for 1 h at −78° C., gaseous formaldehyde was bubbled through the mixture for 5 min and stirring was continued for another hour. The reaction was quenched with saturated sodiumbicarbonate solution (30 ml) and extracted with dichloromethane. Organic phases were pooled, dried with $Na_2SO_4$ and concentrated. Chromatography on silica gel (dichloromethane/methanol, 50:1) yielded the desired product which was crystallized as its HCl-salt from ethanol/ethyl acetate. 65 mg (25%) 7-benzyl-3,3-bis-hydroxymethyl-1-phenyl-1,7-diaza-spiro[3.5]nonan-2-one hydrochloride (1:1) as a colorless solid, m.p.>250° C. and MS: m/e=367.2 ($M^+$+H).

EXAMPLE ag
(RS)-7-Benzyl-3-hydroxymethyl-1-phenyl-1,7-diaza-spiro[3.5]nonan-2-one hydrochloride (1:1)

The title compound, m.p.>117° C. dec. and MS: m/e=337.2 ($M+H^+$) was prepared as byproduct of example af. 60 mg (25%) (RS)-7-benzyl-3-hydroxymethyl-1-phenyl-1,7-diaza-spiro[3.5]nonan-2-one hydrochloride (1:1) as a colorless solid, m.p.>117° C. dec. and MS: m/e=337.2 ($M^+$+H).

EXAMPLE ah
3,3-Bis-hydroxymethyl-1-phenyl-1,7-diaza-spiro[3.5]nonan-2-one hydrochloride (1:1)

The title compound, m.p.>250° C. and MS: m/e=277.2 ($M+H^+$) was prepared in accordance with the general method of example ab from 7-benzyl-3,3-bis-hydroxymethyl-1-phenyl-1,7-diaza-spiro[3.5]nonan-2-one.

EXAMPLE ai
(RS)-3-Hydroxymethyl-1-phenyl-1,7-diaza-spiro[3.5]nonan-2-one

The title compound, a yellow oil, MS: m/e=247.3 ($M+H^+$) was prepared in accordance with the general method of example ah from (RS)-7-benzyl-3-hydroxymethyl-1-phenyl-1,7-diaza-spiro[3.5]nonan-2-one.

EXAMPLE A

| Tablets of the following composition are manufactured in the usual manner | |
|---|---|
| | mg/tablet |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

| Capsules of the following composition are manufactured | |
|---|---|
| | mg/capsule |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

| Suppositories of the following composition are manufactured | |
|---|---|
| | mg/supp. |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into

What is claimed is:

1. Compounds of the general formula I

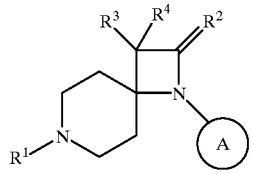

wherein
- $R^1$ is $C_{6-12}$-cycloalkyl, which is unsubstituted or substituted by lower alkyl or C(O)O lower alkyl, indan-1-yl or indan-2-yl, which is unsubstituted or substituted by lower alkyl; acenaphthen-1-yl; bicyclo[3.3.1]non-9-yl, octahydro-inden-2-yl; 2,3-dihydro-1H-phenalen-1-yl; 2,3,3a,4,5,6-hexahydro-1H-phenalen-1-yl, decahydro-azulen-2-yl; bicyclo[6.2.0]dec-9-yl; decahydro-naphthalen-1-yl, decahydro-naphthalen-2-yl; tetrahydro-naphthalen-1-yl, tetrahydro-naphthalen-2-yl or 2-oxo-1,2-diphenyl-ethyl;
- $R^2$ is =O or hydrogen,
- $R^3$ is hydrogen, isoindolyl-1,3-dione, lower alkoxy, lower alkyl, amino, benzyloxy, —$CH_2OR^5$ or —$CH_2N(R^5)_2$;
- $R^4$ is hydrogen or —$CH_2OR^5$;
- $R^5$ is hydrogen or lower alkyl;

is cyclohexyl or phenyl, which is unsubstituted or substituted by lower alkyl, halogen or alkoxy;
racemic mixtures and their corresponding enantiomers and pharmaceutically acceptable acid addition salts thereof.

2. A compound according to claim 1, wherein $R^1$ is $C_{6-9}$-cycloalkyl or decahydro-naphthalen-2-yl.

3. A compound according to claim 2, 3,3-bis-hydroxymethyl-7-(cis-4-isopropyl-cyclohexyl)-1-phenyl-1,7-diaza-spiro-[3.5]nonane-2-one.

4. A compound according to claim 2, 7-(cis-4-isopropyl-cyclohexyl)-1-phenyl-1,7-diaza-spiro[3.5]nonan-2-one.

5. A compound according to claim 2, 7-(cis-4-isopropyl-cyclohexyl)-1-phenyl-1,7-diaza-spiro[3.5]nonane.

6. A compound according to claim 2, 7-cyclononyl-1-phenyl-1,7-diaza-spiro[3.5]nonan-2-one.

7. A compound according to claim 2, 7-cyclononyl-1-phenyl-1,7-diaza-spiro[3.5]nonane.

8. A compound according to claim 2, 7-cyclooctyl-1-phenyl-1,7-diaza-spiro[3.5]nonan-2-one.

9. A compound according to claim 2, 7-cycloheptyl-1-phenyl-1,7-diaza-spiro[3.5]nonan-2-one.

10. A compound according to claim 2, (2RS,4aSR,8aRS)-7-(decahydro-naphthalen-2-yl)-1-phenyl-1,7-diaza-spiro[3.5]nonan-2-one.

11. A pharmaceutical composition comprising a therapeutically effective amount of a compound of formula I

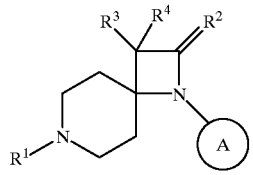

wherein
- $R^1$ is $C_{6-12}$-cycloalkyl, optionally substituted by lower alkyl or C(O)O lower alkyl, indan-1-yl or indan-2-yl, optionally substituted by lower alkyl; acenaphthen-1-yl; bicyclo[3.3.1]non-9-yl, octahydro-inden-2-yl; 2,3-dihydro-1H-phenalen-1-yl; 2,3,3a,4,5,6-hexahydro-1H-phenalen-1-yl, decahydro-azulen-2-yl; bicyclo[6.2.0]dec-9-yl; decahydro-naphthalen-1-yl, decahydro-naphthalen-2-yl; tetrahydro-naphthalen-1-yl, tetrahydro-naphthalen-2-yl or 2-oxo-1,2-diphenyl-ethyl;
- $R^2$ is =O or hydrogen,
- $R^3$ is hydrogen, isoindolyl-1,3-dione, lower alkoxy, lower alkyl, amino, benzyloxy, —$CH_2OR^5$ or —$CH_2N(R^5)_2$;
- $R^4$ is hydrogen or —$CH_2OR^5$;
- $R^5$ is hydrogen or lower alkyl;

is cyclohexyl or phenyl, optionally substituted by lower alkyl, halogen or alkoxy;
as well as pharmaceutically acceptable salts thereof and a pharmaceutically acceptable carrier.

12. A method of treating diseases in mammals related to the orphanin FQ receptor comprising administering to said mammal a compound of the formula I wherein
- $R^1$ is $C_{6-12}$-cycloalkyl, optionally substituted by lower alkyl or C(O)O lower alkyl, indan-1-yl or indan-2-yl, optionally substituted by lower alkyl; acenaphthen-1-yl; bicyclo[3.3.1]non-9-yl, octahydro-inden-2-yl; 2,3-dihydro-1H-phenalen-1-yl; 2,3,3a,4,5,6-hexahydro-1H-phenalen-1-yl, decahydro-azulen-2-yl; bicyclo[6.2.0]dec-9-yl; decahydro-naphthalen-1-yl, decahydro-naphthalen-2-yl; tetrahydro-naphthalen-1-yl, tetrahydro-naphthalen-2-yl or 2-oxo-1,2-diphenyl-ethyl;
- $R^2$ is =O or hydrogen,
- $R^3$ is hydrogen, isoindolyl-1,3-dione, lower alkoxy, lower alkyl, amino, benzyloxy, —$CH_2OR^5$ or —$CH_2N(R^5)_2$;
- $R^4$ is hydrogen or —$CH_2OR^5$;

$R^5$ is hydrogen or lower alkyl;

is cyclohexyl or phenyl, optionally substituted by lower alkyl, halogen or alkoxy;
as well as pharmaceutically acceptable salts thereof and a pharmaceutically acceptable carrier in an amount which is effective for treating said disease.

13. A process for preparing a compound of formula I as defined in claim 1, comprising
reductively aminating a compound of formula

     II with a compound of formula

III

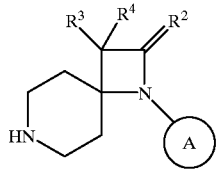

wherein
$R^1$ is $C_{6-12}$-cycloalkyl, optionally substituted by lower alkyl or C(O)O lower alkyl, indan-1-yl or indan-2-yl, optionally substituted by lower alkyl; acenaphthen-1-yl; bicyclo[3.3.1]non-9-yl, octahydro-inden-2-yl; 2,3-dihydro-1H-phenalen-1-yl; 2,3,3a,4,5,6-hexahydro-1H-phenalen-1-yl, decahydro-azulen-2-yl; bicyclo[6.2.0]dec-9-yl; decahydro-naphthalen-1-yl, decahydro-naphthalen-2-yl; tetrahydro-naphthalen-1-yl, tetrahydro-naphthalen-2-yl or 2-oxo-1,2-diphenyl-ethyl;

$R^2$ is =O or hydrogen, $R^3$ is hydrogen, isoindolyl-1,3-dione, lower alkoxy, lower alkyl, amino, benzyloxy, —CH$_2$OR$^5$ or —CH$_2$N(R$^5$)$_2$;

$R^4$ is hydrogen or —CH$_2$OR$^5$;

$R^5$ is hydrogen or lower alkyl;

I

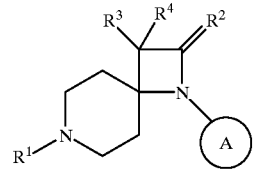

is cyclohexyl or phenyl, optionally substituted by lower alkyl, halogen or alkoxy.

14. The process of claim 13 wherein said amination is performed by stirring the compound of formula II with the compound of formula III in the presence of a dehydrating agent and in the presence of molecular sieves in an inert solvent at reflux temperature.

15. The process of claim 14 wherein said inert solvent is toluene or tetrahydrofuran.

16. The process of claim 13 further comprising converting a racemic mixture of a compound of formula I into its enantomeric components thus obtaining substantially optically pure compounds.

17. The process of claim 13 further comprising converting a compound of formula I into a pharmaceutically acceptable salt thereof.

* * * * *

UNITED STATES PATENT AND TRADEMARK OFFICE
CERTIFICATE OF CORRECTION

PATENT NO. : 6,113,527
DATED : September 5, 2000
INVENTOR(S) : Geo Adam et al.

It is certified that error appears in the above-identified patent and that said Letters Patent is hereby corrected as shown below:

In claim 13, column 38, lines 10-20, delete

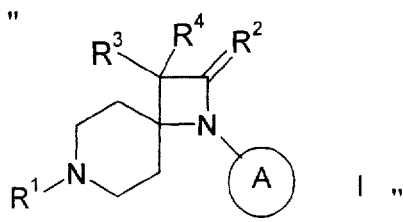

and insert --  -- before the word "is" in line 21.

Signed and Sealed this

Fifteenth Day of May, 2001

Attest:

NICHOLAS P. GODICI

Attesting Officer   Acting Director of the United States Patent and Trademark Office